US006855662B2

(12) United States Patent
Katsube et al.

(10) Patent No.: US 6,855,662 B2
(45) Date of Patent: Feb. 15, 2005

(54) CATALYST FOR PREPARING FLUORINE-CONTAINING ALCOHOL COMPOUND AND A PROCESS FOR PREPARATION OF FLUORINE-CONTAINING ALCOHOL COMPOUND

(75) Inventors: Toshiyuki Katsube, Settsu (JP); Yuuki Matsuda, Settsu (JP); Jun Miki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/242,688

(22) Filed: Sep. 13, 2002

(65) Prior Publication Data

US 2003/0100804 A1 May 29, 2003

(30) Foreign Application Priority Data

Sep. 13, 2001 (JP) ........................................ 2001-277550

(51) Int. Cl.[7] ................................................ B01J 27/13
(52) U.S. Cl. ........................ 502/230; 568/842; 568/801
(58) Field of Search ......................... 502/230; 568/842, 568/801

(56) References Cited

U.S. PATENT DOCUMENTS

| | | | | | |
|---|---|---|---|---|---|
| 4,528,185 A | * | 7/1985 | Kraft et al. | ............... | 424/78.26 |
| 4,614,728 A | * | 9/1986 | Hirai et al. | .................. | 502/244 |
| 5,087,775 A | * | 2/1992 | Gassen et al. | ............... | 568/842 |
| 5,118,651 A | | 6/1992 | Gubelmann et al. | | |
| 5,268,512 A | * | 12/1993 | Miki et al. | ................... | 568/801 |
| 5,756,802 A | * | 5/1998 | Li et al. | ...................... | 558/319 |
| 5,958,367 A | * | 9/1999 | Ying et al. | .................... | 423/701 |
| 6,001,768 A | * | 12/1999 | Buysch et al. | ............... | 502/230 |
| 6,093,674 A | * | 7/2000 | Windisch et al. | ........... | 502/154 |
| 6,187,969 B1 | * | 2/2001 | Yamaguchi et al. | ........ | 568/842 |
| 6,194,591 B1 | * | 2/2001 | Grey et al. | ................. | 549/533 |
| 6,342,200 B1 | * | 1/2002 | Rouleau et al. | ............. | 423/709 |
| 6,465,387 B1 | * | 10/2002 | Pinnavaia et al. | .......... | 502/158 |
| 6,514,479 B1 | * | 2/2003 | Merlen et al. | ............... | 423/705 |
| 6,528,034 B1 | * | 3/2003 | Pinnavaia et al. | .......... | 423/335 |
| 6,548,040 B1 | * | 4/2003 | Rouleau et al. | ............. | 423/705 |
| 6,548,445 B1 | * | 4/2003 | Buysch et al. | ............... | 502/230 |
| 6,566,569 B1 | * | 5/2003 | Chen et al. | ................. | 585/324 |
| 6,664,430 B1 | * | 12/2003 | Miki et al. | ................... | 568/842 |
| 6,703,342 B1 | * | 3/2004 | Lok | ........................... | 502/346 |

FOREIGN PATENT DOCUMENTS

| JP | WO 0069557 A1 * 11/2000 | ............ B01J/29/85 |
|---|---|---|
| WO | WO00/69557 | 11/2000 |

OTHER PUBLICATIONS

Hawley's Condensed Chemical Dictionary Online, definitions of "coordination compound" and "cobaltammine".*

* cited by examiner

Primary Examiner—Mark L. Bell
Assistant Examiner—Jennine M. Brown
(74) Attorney, Agent, or Firm—Armstrong, Kratz, Quintos, Hanson & Brooks, LLP

(57) ABSTRACT

A catalyst for preparing a fluorine-containing alcohol compounds, the catalyst is obtained by supporting an ammine complex containing at least one component selected from the group consisting of the elements in Group 1B, Group 2B, Group 6A, Group 7A and Group 8 of the periodic table on at least one complex oxide selected from the group consisting of Si—Al complex oxide, Al—P complex oxides and Si—Al—P complex oxides.

10 Claims, No Drawings

CATALYST FOR PREPARING FLUORINE-CONTAINING ALCOHOL COMPOUND AND A PROCESS FOR PREPARATION OF FLUORINE-CONTAINING ALCOHOL COMPOUND

BACKGROUND OF THE INVENTION (1) Field of the Invention

The present invention relates to a process for preparing a fluorine-containing alcohol compound and to a catalyst used in the process.

(2) Description of Related Art

Japanese Unexamined Patent Publication No. 1992-506507 proposes a process for preparing a fluorine-containing alcohol compound having water repellency and oil repellency by treating a halogenated alkyl on a catalyst to convert it into an alcohol. However, this process has the drawbacks of using a gas phase reaction at a temperature as high as 400 to 600° C. and of involving a low degree of conversion and selectivity.

The inventors conducted extensive research to overcome the foregoing drawbacks. Consequently, the inventors found a process for preparing a fluorine-containing alcohol compound in a high yield by treating a halogenated alkyl at a relatively low reaction temperature on a catalyst which has an element of a specific group of the periodic table, an ion of such an element, an oxide, hydroxide, salt or the like containing such an element or elements supported on a specific complex oxide (WO00/69557). However, it was found that this process should remains to be improved in the catalytic activity varying with time.

A primary object of the present invention is to provide a process for preparing a fluorine-containing alcohol compound without using special reagents or solvents under relatively moderate reaction conditions over a prolonged time in a high yield.

SUMMARY OF THE INVENTION

The inventors of the invention improved the process for preparing a catalyst and surprisingly found the following. At least one component selected from the group consisting of the elements in Group 1B, Group 2B, Group 6A, Group 7A and Group 8 of the periodic table is made into an ammine complex, and the ammine complex is made to be supported on at least one complex oxide selected from the group consisting of Si—Al complex oxides, Al—P complex oxides and Si—Al—P complex oxides, thereby producing a catalyst which is highly reproducible, high in catalytic activity and unlikely to lower in catalytic activity. The inventors also discovered that a fluorine-containing alcohol compound can be prepared by using said catalyst without using special reagents or solvents under relatively moderate reaction conditions (e.g. relatively low reaction temperature) over a prolonged time with a high yield and high selectivity. The present invention was completed based on these novel findings.

Specifically, the present invention provides the following catalysts for preparing a fluorine-containing alcohol compound and the following processes for preparing a fluorine-containing alcohol compound.

1. A catalyst for preparing a fluorine-containing alcohol compound, the catalyst obtained by supporting at least one ammine complex of an element selected from the elements in Group 1B, Group 2B, Group 6A, Group 7A and Group 8 of the periodic table on at least one complex oxide selected from the group consisting of Si—Al complex oxides, Al—P complex oxides and Si—Al—P complex oxides.

2. The catalyst according to item 1, wherein the complex oxide is an oxide having a zeolite structure.

3. The catalyst according to item 1, wherein the ammine complex is at least one member selected from the group consisting of ammine complexes of Cu, Ag, Ni, Co, Fe, Hg and Pd.

4. A process for preparing a fluorine-containing alcohol compound represented by the formula (II):

$$Rf—(CH_2)_nOH \quad (II)$$

[wherein Rf represents a perfluoroalkyl group or a polyfluoroalkyl group, and n is an integer of from 1 to 5], the process comprising the step of reacting water with a halogenated fluorine compound represented by the formula (I):

$$Rf—(CH_2)_nX \quad (I)$$

[wherein Rf is as defined above, X represents I, Br or Cl and n is as defined above] in the presence of the catalyst as defined in item 1.

5. The process according to item 4, wherein the reaction between the halogenated fluorine compound of the formula (I) and water is carried out in an atmosphere of an oxygen-containing gas.

6. The process according to item 4, wherein the reaction is carried out under pressure.

DETAILED DESCRIPTION OF THE INVENTION

The catalyst for preparing a fluorine-containing alcohol compound for use in the present invention is a catalyst obtained by supporting an ammine complex formed from at least one component selected from the group consisting of elements in Group 1B, Group 2B, Group 6A, Group 7A and Group 8 of the periodic table, ions of the element, oxides containing the element, hydroxides containing the element and salts containing the element on at least one complex oxide selected from the group consisting of Si—Al complex oxides, Al—P complex oxides and Si—Al—P complex oxides.

Among these elements, examples of the elements in Group 1B include Cu, Ag and Au; examples of the elements in Group 2B include Zn, Cd and Hg; examples of the elements in Group 6A include Cr, Mo and W; examples of the elements in Group 7A include Mn, Tc and Re; examples of the elements in Group 8 include Ni, Co, Fe, Ru, Rh, Pd, Pt and Ir and the like. Among them, Cu, Ag, Ni, Co, Fe, Hg and Pd are preferred in the present invention.

In the present invention, these elements may be made into an ammine complex, or the ions of these elements, and oxides, hydroxides, salts or the like containing one or more of these elements may be also made into an ammine complex, and supported on the above-mentioned specific complex oxide.

The oxides may be those containing one or more of the above elements, and the valence of the element is not limited. Examples of oxides include CuO and $Cu_2O$. The hydroxides may be those containing one or more of the above elements, and the valence of the element is not limited. Examples of hydroxides include CuOH and $Cu(OH)_2$. The ions may be those of the above elements, and the charge number of the useful ion is not limited. Examples of ions include $Cu^+$ and $Cu^{2+}$. Examples of the useful salts include sulfate, nitrates, carbonates acetates and the like. Example of salts include $CuSO_4$ and $Cu(CH_3COO)_2$.

An ammine complex is a complex having ammonia as a ligand of metal ion. Examples include $[Cu(NH_3)_4]^{2+}$, $[Ag(NH_3)_2]^+$, $[Co(NH_3)_6]^{2+}$, $[Fe(NH_3)_6]^{2+}$, $[Ni(NH_3)_6]^{2+}$, $[Pd(NH_3)_4]^{2+}$, $[Hg(NH_3)]^{2+}$ and the like.

The counter ions of ammine complex are not limited and include, for example, chlorine ion.

An ammine complex can be prepared by conventional methods comprising passing dry ammonia through a halide of the above-mentioned element or treating a halide of the above-mentioned element with liquid ammonia. When using a transition metal (among said elements, the elements in Group 8 and Group 1B of the periodic table), e.g., an aqueous solution of the salt thereof may be treated with ammonia (Encyclopedia Chimica, Kyoritsu Shuppan Co. Ltd., Sep. 20, 1997, reduced-size edition, $36^{th}$ issue, Vol.1, p.525). More specifically, about 0.1 to about 100 g of an aqueous solution of about 30 mass % of ammonia is added to about 200 to about 400 g of an aqueous solution of about 0.01 to about 3 mole % of salt of said metal. The mixture is stirred for about 1 to about 10 minutes when required. This procedure is carried out approximately at room temperature.

When an ammine complex is prepared from oxides or hydroxides of said elements, it can be obtained by the similar method for preparing an ammine complex from a salt.

An ammine complex prepared from said element can be obtained by treating the element with an acid in the conventional manner to give a salt and treating the salt with ammonia in the same manner as above.

An ammine complex prepared from ions of said element can be obtained by preparing an aqueous solution of the element in the conventional manner and treating the solution with ammonia.

In the specification, a metal element component which is supported on a carrier utilizing an ammine complex may be referred to collectively as "supported component".

The catalyst of the present invention uses at least one complex oxide selected from the group consisting of Si—Al complex oxides, Al—P complex oxides and Si—Al—P complex oxides as a carrier to support the above-mentioned supported component.

Examples of such complex oxides include silica-alumina, synthetic silica-alumina zeolite, natural silica-alumina zeolite, aluminum phosphate, synthetic aluminum phosphate zeolite, synthetic Si—Al—P zeolite (SAPO) and the like.

Using a catalyst having the above-mentioned supported component supported on at least one complex oxide selected from the group consisting of Si—Al complex oxides, Al—P complex oxides and Si—Al—P complex oxides, the degree of conversion of raw material, selectivity of the desired product, etc. can be improved in the below-described process for preparing a fluorine-containing alcohol compound. Among these complex oxides, use of an oxide having a zeolite structure particularly increases selectivity of alcohol.

The method to support the above ammine complex of said element on the above-described carrier is not particularly limited, and includes, for example, conventional impregnation method. The forms of the complex oxide to be immersed in an ammine complex solution include, but are not limited to, powders, granules, tablets and honeycombs, among others. For instance, when using SAPO-11 zeolite as a Si—Al—P complex oxide, the above-mentioned supported component can be supported on the complex oxide by immersing the zeolite in an aqueous solution of an ammine complex to impregnate the zeolite with the solution, and then drying it, optionally followed by calcining it. There is no limitation on calcining conditions. The calcining conditions can be suitably determined according to the kind of ammine complex to be used without limitation insofar as the conditions allow removal of most part of water adhering to or adsorbed on the carrier and permit removal of part or most part of volatile components. For example, calcining can be conducted usually for about 1 to about 10 hours, preferably about 2 to about 3 hours in an oxidizing atmosphere such as air or in the presence of nitrogen, argon, carbon dioxide or the like. The calcining temperature is in the range of about 100 to about 500° C., preferably about 200 to about 400° C.

The supported component when calcined is finally caused to exist as an oxide, hydroxide or ions on the carrier without limitation on the valence of the element.

In a catalyst containing the above supported component supported on the complex oxide, the proportion of the supported component calculated as the metal oxide, per the total catalyst is suitably about 1 to about 30 mass %, preferably about 5 to about 15 mass %.

By use of an ammine complex as in the invention, the supported component is allowed to uniformly disperse on the surface of at least one complex oxide selected from the group consisting of Si—Al complex oxides, Al—P complex oxides and Si—Al—P complex oxides. Thereby a catalyst having a high specific surface area can be produced without the collapse of crystal structure of at least one of Si—Al complex oxides, Al—P complex oxides and Si—Al—P complex oxides, thus with a high activity and a high reproducibility.

The above-mentioned supported components can be used either alone or in combination.

The catalyst of the invention is preferably one containing elements selected from the group consisting of Cu, Ag, Ni, Co, Fe, Hg and Pd, among the above supported components. The catalyst containing an supported component having Cu and Ni shows a high selectivity of desired product. The catalyst containing an supported component having Ag allows a reaction at a relatively low temperature. The catalyst containing an supported component having Fe shows a high catalytic activity.

Next, the process for preparing a fluorine-containing alcohol compound using the above-mentioned catalyst will be explained.

In the process of the present invention, a fluorine-containing alcohol compound represented by formula (II):

Rf—(CH$_2$)$_n$OH (II)

[wherein Rf represents a perfluoroalkyl group or a polyfluoroalkyl group and n is an integer of from 1 to 5] can be prepared by reacting water with a halogenated fluorine compound represented by formula (I):

Rf—(CH$_2$)$_n$X (I)

[wherein Rf and n are as defined above and X represents I, Br or Cl] in the presence of the above-mentioned catalyst.

In the compound of formula (I) and the compound of the formula (II), examples of the perfluoroalkyl group represented by Rf include $C_1$—$C_{20}$ straight-chain or branched-chain perfluoroalkyl groups. Specific examples include $CF_3$, $C_2F_5$, (n- or iso)$C_3F_7$, (n-, iso, sec- or tert-)$C_4F_9$, $CF_3(CF_2)_{m-}$ [m is an integer from 4 to 19], among others.

In the compound of formula (I) and the compound of the formula (II), examples of the polyfluoroalkyl group are not limited insofar as the groups are those having at least two fluorine atoms. Examples include $HCF_2(CF_2)_p$ [p is an integer from 1 to 19], among others. Specific examples include $HCF_2CF_2$, $HCF_2CF_2CF_2CF_2$, $HCF_2CF_2CF_2CF_2CF_2CF_2$, etc.

The reaction between the halogenated fluorine compound represented by formula (I) and water can be carried out by a batch process or a continuous process. The reactor for this reaction is not particularly limited, and a gas phase continuous reactor equipped with reaction vessel such as fixed bed, fluidized bed, moving bed, etc., or a batch reactor may be used.

The process for reacting the halogenated fluorine compound and water by gas phase continuous reaction comprises, for example, the steps of placing a stainless-steel reaction tube filled with the catalyst of the present invention in an electric heating furnace, heating the catalyst layer to a reaction temperature, introducing the raw material and water into a vaporizer at a constant rate using a plunger pump or the like, conveying the vaporized gas to the catalyst layer by air or like carrier gases to react the vaporized gas, and recovering a reaction product with a subsequent trap or the like. Favorable reaction conditions may somewhat vary depending on the kind of catalyst used and can be suitably determined. The reaction temperature may be about 120 to 400° C., preferably about 150 to 300° C. The reaction can be carried out under atmospheric pressure or increased pressure. Particularly, when reacting under increased pressure, preferably under a pressure of 0.2 MPa or higher, more preferably 0.3 MPa or higher, even more preferably 0.4 MPa or higher, particularly preferably 0.5 MPa or higher, alcohol selectivity can be increased. The upper limit of pressure is not limited but it is usually 0 to about 10 MPa, preferably about 0.1 to about 1 MPa. The molar ratio of the halogenated fluorine compound to water (halogenated fluorine compound: water) is desirably about 1:0.2 to 200, more desirably about 1:1 to 50. W/F (contact time) may be about 0.1 to 10 g·sec/ml.

When the reaction is conducted by the batch process, it can be conducted, for example, by the method comprising the following steps: placing the raw material, water and the catalyst in an autoclave or like pressure vessel; and heating the mixture with a heater to a reaction temperature to allow the mixture to react for a certain period of time with stirring. Preferable reaction conditions may somewhat vary depending on the kind of catalyst used but can be suitably determined. The reaction temperature may be about 120 to 400° C., preferably about 150 to 300° C. The molar ratio of the halogenated fluorine compound to water (halogenated fluorine compound: water) is desirably about 1:0.2 to 200, more desirably 1:1 to 50. The weight ratio of the halogenated fluorine compound to the catalyst (halogenated fluorine compound: catalyst) may be about 1:0.01 to 1. The reaction time may be about an hour to about 100 hours.

As for the reaction atmosphere, the reaction may be conducted in an atmosphere including nitrogen, helium, carbon dioxide or like inert gases, air or like oxygen-containing gases or oxygen-containing gas diluted with an inert gas, among others. In particular, a reaction conducted in an atmosphere of air or like oxygen-containing gas accelerates the oxidation of HX formed by the reaction to $X_2$, thereby facilitating the recovery of $X_2$. Therefore it is preferable to conduct the reaction in an oxygen-containing gas. The recovered $X_2$ can be used as a raw material in the production process of the starting compound represented by the above formula (I): $Rf—(CH_2)_nX$. Particularly when the formed $X_2$ is $I_2$, iodine can be advantageously recovered without troublesome and environmentally unfavorable treatments such as oxidation by chlorine which is heretofore necessary for recovering iodine from a waste liquid containing iodide ions. The thus recovered iodine is a very important resource which can be collected by distillation, sublimation or other methods. Such iodine can be used as a raw material for preparing the staring compound for use in the process of the present invention, i.e., halogenated fluorine compound.

In the continuous reaction, the supply of air and like oxygen-containing gas together with the raw material and water can prevent catalyst activity from decreasing. In this case, the amount of oxygen is preferably at least about ¼ mole per mole of the halogenated fluorine compound. The upper limit of oxygen amount is not limited. Preferably it is about 50 moles or less per mole of halogenated fluorine compound.

According to the preparation process of the present invention, by reacting water and the halogenated fluorine compound in the presence of the specific catalyst, the fluorine-containing alcohol compound can be prepared at a relatively low reaction temperature over a prolonged time in a high yield.

BEST MODE FOR CARRYING OUT THE INVENTION

Below, the present invention is explained in further detail with reference to Examples. However, the present invention is not limited to these Examples.
Preparation of Catalyst

PREPARATION EXAMPLE 1

$CuSO_4·5H_2O$ (50 g) was dissolved in 250 g of pure water, and 50 g of an aqueous solution of 30 mass % of ammonia was added, giving an aqueous solution of deep blue copper ammine complex. 50 g of commercially available Si—Al—P zeolite (SAPO-11) was added to the copper ammine complex solution to impregnate the zeolite with the aqueous solution of copper ammine complex. The pressure was reduced for deaeration for 30 minutes. The solution was allowed to stand at room temperature for 10 hours and filtrated. The procedure was repeated using the same amount of new copper ammine complex solution. The aqueous solution was filtrated and vacuum-dried at 100° C. for 3 hours.

Subsequently, the dried product was calcined in the air within a muffle furnace at 300° C. for 3 hours to undergo the reaction described below in Examples. The calcined catalyst had 6 mass % of a supported copper compound, calculated as CuO.

PREPARATION EXAMPLE 2

The same procedure as in Preparation Example 1 was conducted with the exception of using 34 g of $CuCl_2·2H_2O$ in place of 50 g of $CuSO_4·5H_2O$ to give a catalyst. The catalyst had 6 mass % of copper compound supported on the carrier, calculated as CuO.

PREPARATION EXAMPLE 3

The same procedure as in Preparation Example 1 was conducted with the exception of using 40 g of $Cu(CH_3·COO)_2·H_2O$ in place of 50 g of $CuSO_4·5H_2O$ to give a catalyst. The catalyst had 6 mass % of copper compound supported on the carrier, calculated as CuO.

PREPARATION EXAMPLE 4

50 g of $CuSO_4·5H_2O$ was dissolved in 300 g of pure water to give an aqueous solution of copper sulfate. A commercially available Si—Al—P zeolite (50 g) (SAPO-11) was added to the aqueous solution of copper sulfate to impregnate the zeolite with the aqueous solution of copper sulfate. The pressure was reduced for deaeration for 30 minutes. The solution was allowed to stand at room temperature for 10 hours and filtrated. The procedure was repeated using the same amount of new copper sulfate solution. The aqueous solution was filtrated and vacuum-dried at 100° C. for 3 hours.

Subsequently, the dried product was calcined in the air within a muffle furnace at 300° C. for 3 hours to undergo the reaction described below in Examples. The calcined catalyst had 6 mass % of a supported copper compound, calculated as CuO.

PREPARATION EXAMPLE 5

The same procedure as in Preparation Example 4 was conducted with the exception of using 34 g of $CuCl_2 \cdot 2H_2O$ in place of 50 g of $CuSO_4 \cdot 5H_2O$ to give a catalyst. The catalyst had 6 mass % of copper compound supported on the carrier, calculated as CuO.

PREPARATION EXAMPLE 6

The same procedure as in Preparation Example 4 was conducted with the exception of using 40 g of $Cu(CH_3COO)_2 \cdot H_2O$ in place of 50 g of $CuSO_4 \cdot 5H_2O$ to give a catalyst. The catalyst had 6 mass % of copper compound supported on the carrier, calculated as CuO.

EXAMPLE 1

The catalyst of Preparation Example 1 (10 g) was packed into a stainless-steel reaction tube having an inside diameter of 10 mm and length of 250 mm, and was heated to 280° C. with a heater. $CF_3CF_2(CF_2CF_2)_3CH_2CH_2I$ and water were introduced into a vaporizer (preheat phase) at a rate of 2.5 g/hr and 12 g/hr, respectively, with a plunger pump and were vaporized. Air was introduced into the reaction tube as a carrier gas at a rate of 35 ml/min. The vaporized gases were carried to the catalyst by the air to cause a catalytic reaction on the catalyst. Reaction products were recovered with an ice trap and a dry ice/methanol trap provided at the outlet of the reaction tube. The analysis of the products by gas chromatography revealed that a fluorine-containing alcohol ($CF_3CF_2(CF_2CF_2)_3CH_2CH_2OH$) was formed at the degree of conversion of 99% and selectivity of 97% (1 hour after start of the reaction); that a fluorine-containing alcohol was formed at the degree of conversion of 99% and selectivity of 98% (10 hours after start of the reaction); and that a fluorine-containing alcohol was formed at the degree of conversion of 99% and selectivity of 97% (1,000 hours after start of the reaction).

EXAMPLES 2 AND 3

Reactions were conducted in a manner similar to Example 1 using the catalysts of the above Preparation Examples 2 and 3. The results of analysis are shown in Table 1 below.

TABLE 1

| Kind of Catalyst | Example 2 Preparation Example 2 | | Example 3 Preparation Example 3 | |
| --- | --- | --- | --- | --- |
| | Degree of Conversion (%) | Selectivity (%) | Degree of Conversion (%) | Selectivity (%) |
| 1 hour later | 99 | 90 | 99 | 83 |
| 10 hours later | 98 | 90 | 94 | 84 |
| 100 hours later | 99 | 88 | 96 | 89 |
| 1,000 hours later | 99 | 90 | 94 | 87 |

COMPARATIVE EXAMPLES 1 TO 3

Using the catalysts of Preparation Examples 4 to 6, the same reaction as done in Example 1 was carried out. The analysis results are shown in Table 2.

TABLE 2

| Kind of catalyst | Comp. Ex.1 Prep.Ex.4 | | Comp. Ex.2 Prep.Ex.5 | | Comp.Ex.3 Prep.Ex.6 | |
| --- | --- | --- | --- | --- | --- | --- |
| | Degree of Conversion (%) | Selectivity (%) | Degree of Conversion (%) | Selectivity (%) | Degree of Conversion (%) | Selectivity (%) |
| 1 hour later | 98 | 95 | 95 | 95 | 97 | 86 |
| 10 hours later | 98 | 94 | | | 97 | 90 |
| 100 hours later | 97 | 95 | 88 | 85 | 92 | 85 |
| 1,000 hours later | 52 | 95 | 89 | 85 | 55 | 87 |

EXAMPLE 4

The reaction was carried out under increased pressure (0.3 MPa) in the process of Example 1. The analysis results are shown in Table 3.

TABLE 3

| Kind of catalyst | Example 4 Prep. Example 2 | |
| --- | --- | --- |
| | Degree of conversion (%) | Selectivity (%) |
| 1 hour later | 99 | 98 |
| 10 hours later | 99 | 98 |
| 100 hours later | 98 | 98 |
| 1,000 hours later | 99 | 98 |

What is claimed is:
1. A catalyst for preparing a fluorine-containing alcohol compound, comprising:

one or more amine complexes consisting of ammonia and a metal, wherein the nitrogen atom of said ammonia is directly linked to a metal atom to form said ammine complex, said metal atom being selected from the group consisting of the elements in Group 1B, Group 2B, Group 6A, Group 7A and Group 8, of the periodic table, wherein said metal atom is not Pt; and one or more complex oxides selected from the group consisting of an Si—Al complex oxide, an Al—P complex oxides oxide and an Si—Al—P complex oxide, wherein said one or more ammine complexes are supported on said one more complex oxides.

2. The catalyst according to claim 1, wherein said one or more complex oxides have a zeolite structure.

3. The catalyst according to claim 1, wherein said complex oxide is selected from the group consisting of synthetic silica-alumina zeolite, natural silica-alumina zeolite, aluminum phosphate, synthetic aluminum phosphate zeolite, and synthetic S—Al—P zeolite.

4. The catalyst according to claim 1, wherein said metal atom is selected from the group consisting of Cu, Ag, Ni, Co, Fe, Hg and Pd.

5. The catalyst according to claim 1, wherein said me complex is $[Cu(NH_3)_4]^{2+}$.

6. A method for producing a catalyst for preparing a fluorine-containing alcohol compounds comprising;

supporting one or more ammine complexes consisting of ammonia and a metal atom selected from the group consisting of the elements in Group 1B, Group 2B, Group 6A, Group 7A and Group 8 of the periodic table, on one or more complex oxides selected from the group consisting of an Si—Al complex oxide, an Al—P complex oxide and an Si—Al—P complex oxides oxide to give a supported catalyst, wherein said metal atom is not Pt, and wherein the nitrogen atom of said ammonia is directly linked to said metal atom to form said ammine complex.

7. The method according to claim 6, wherein said metal atom is selected from the group consisting of Cu, Ag, Ni, Co, Fe Hg and Pd.

8. The method according to claim 6, wherein said supporting comprises impregnating said one or more ammine complexes on said one or more complex oxides.

9. The method according to claim 6, further comprising calcining the supported catalyst at a temperature within the range of from about 100° C. to about 500° C. in an oxidizing atmosphere or in the presence of nitrogen, argon, and carbon dioxide.

10. A catalyst produced by the method according to claim 9.

* * * * *